United States Patent [19]

Prince et al.

[11] Patent Number: 4,849,693
[45] Date of Patent: Jul. 18, 1989

[54] AUTOMATED MEASUREMENT SYSTEM EMPLOYING EDDY CURRENTS TO ADJUST PROBE POSITION AND DETERMINE METAL HARDNESS

[75] Inventors: James M. Prince, Kennewick; Michael G. Dodson, Richland; Wayne M. Lechelt, Benton City, all of Wash.

[73] Assignee: Battelle Memorial Institute, Richland, Wash.

[21] Appl. No.: 162,020

[22] Filed: Feb. 29, 1988

[51] Int. Cl.$^4$ .................. G01N 27/72; G01R 33/14; G01R 33/12
[52] U.S. Cl. .................. 324/225; 324/227; 324/233; 324/243
[58] Field of Search .............. 324/225, 226, 227, 239, 324/243, 233, 234, 236

[56] References Cited

U.S. PATENT DOCUMENTS 2,846,065  8/1956  Alexander ........................ 324/243
4,727,322  2/1988  Lanchampt et al. ............. 324/225

Primary Examiner—Reinhard J. Eisenzopf
Assistant Examiner—Walter E. Snow
Attorney, Agent, or Firm—Dellett, Smith-Hill & Bedell

[57] ABSTRACT

A system for measuring the hardness of cartridge cases employs an eddy current probe for inducing and sensing eddy currents in each cartridge case. A first component of the sensed signal is utilized in a closed loop system for accurately positioning the probe relative to the cartridge case both in the lift off direction and in the tangential direction, and a second component of the sensed signal is employed as a measure of the hardness. The positioning and measurement are carried out under closed loop microprocessor control facilitating hardness testing on a production line basis.

26 Claims, 6 Drawing Sheets

U.S. Patent    Jul. 18, 1989    Sheet 1 of 6    4,849,693
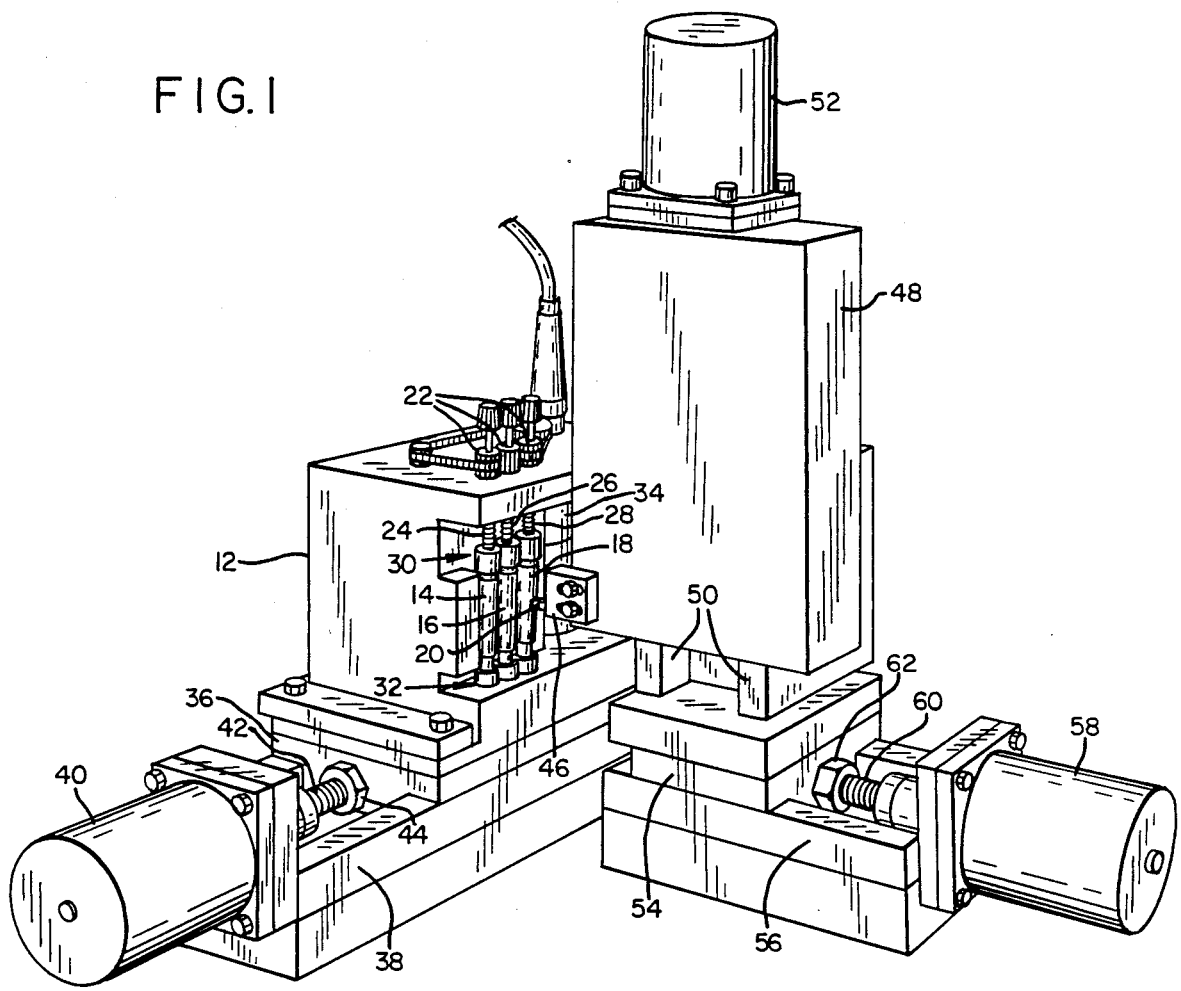
FIG.1
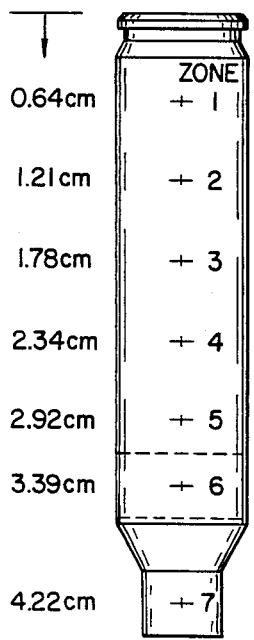
FIG.2
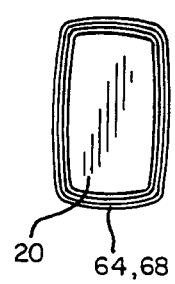
FIG.5
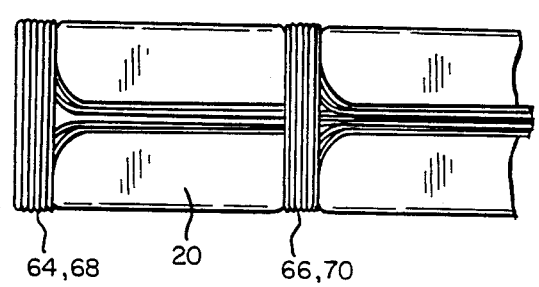
FIG.3
FIG.4

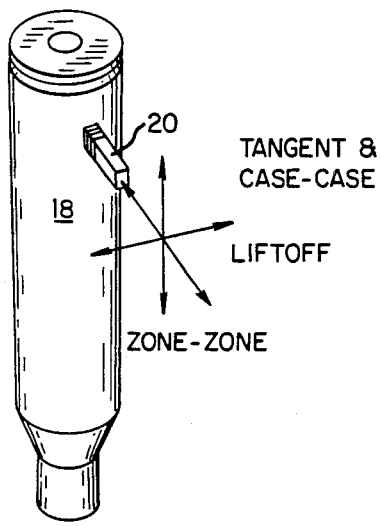
FIG. 6
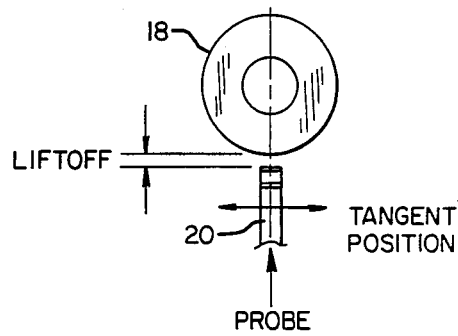
FIG. 7
FIG. 8
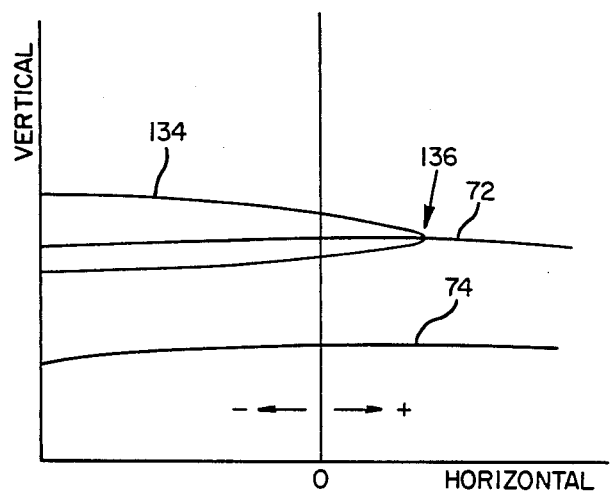
FIG. 9
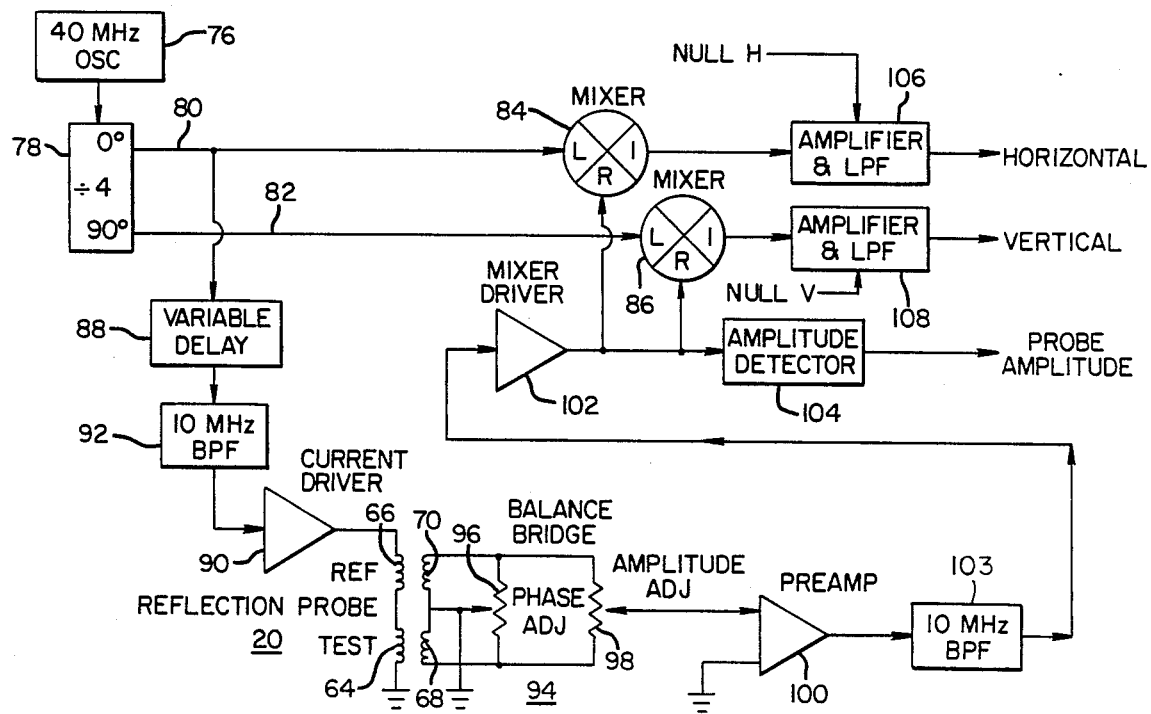

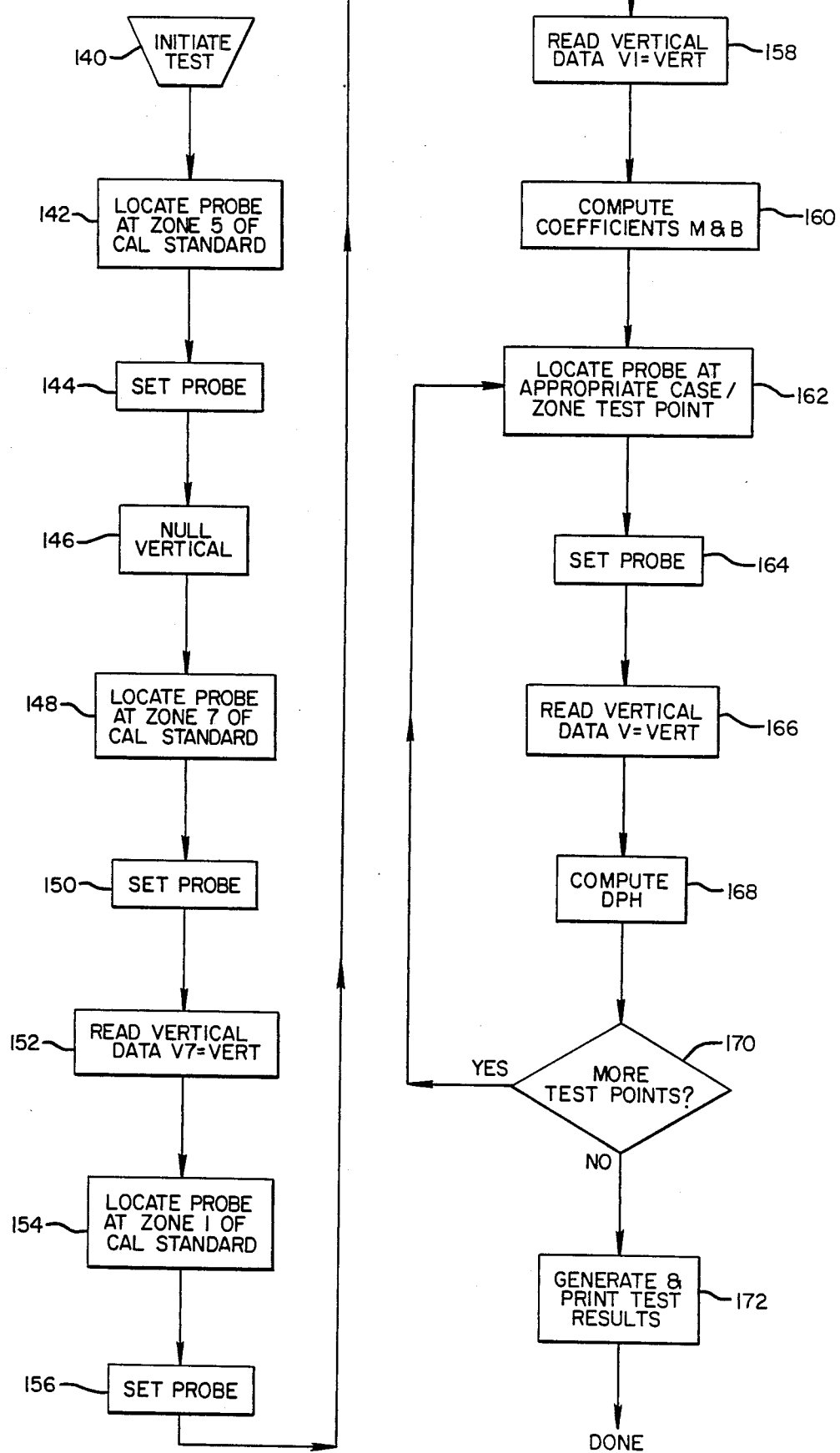

AUTOMATED MEASUREMENT SYSTEM EMPLOYING EDDY CURRENTS TO ADJUST PROBE POSITION AND DETERMINE METAL HARDNESS

BACKGROUND OF THE INVENTION

This invention was made with government support under contract number DE-AC06-76RLO 1830, awarded by the U.S. Department of Energy. The government has certain rights in the invention.

The present invention relates to the measurement of metal hardness and particularly to measurement of the hardness of brass cartridge cases.

In the manufacture of cartridge cases, a correct annealing procedure will result in a product having an acceptable hardness profile over its length. Hardness needs to be monitored frequently during production in order to insure that proper annealing is taking place. Unfortunately, the conventional method of measuring hardness of cartridge cases comprises diamond-point indentation testing which requires at least 15 seconds to perform a measurement. During this time period, three hundred cases will have been produced on a typical cartridge case manufacturing line. Since it is also desirable to average hardness data over several samples before concluding annealer adjustment is required, it can be seen that by the time improper annealing has been detected, a large quantity of cases of the wrong hardness may have been produced.

Metal hardness can be measured by methods other than diamond-point testing. For instance, non-contact eddy current testing instruments and acoustic instruments are commercially available for testing hardness. However, conventional instruments cannot provide adequate measurement resolution and measurement repeatability on a rapid basis, especially for a thin walled curved surface geometry such as exemplified by a 5.56 mm. M-193 brass cartridge case.

SUMMARY OF THE INVENTION

According to the present invention, a system for accurately measuring metal hardness of a curved surface sample employs a non-contact eddy current sensor that is accurately and rapidly positioned. High amplification processing of a high frequency signal is utilized to assure correct measurement of a thin walled case whereby sensor-to-material positioning needs to be very repeatable. According to the present invention, an eddy current sensor signal is employed not only as a measure of hardness of the case under test, but also for positioning the sensor relative to the case in an automatic closed-loop system. As a result, not only is accuracy achieved, but also the speed with which the hardness of cartridge cases is measured is increased by at least an order of magnitude.

In accordance with a feature of the present invention, a non-contact eddy current sensor output is separated into orthogonal components which are representative of the position of the sample case under test, and the conductivity of the sample case. The signal component representing sample position is employed in a closed loop feedback system for accurately locating the sensor relative to the sample. When the sensor is accurately positioned, a remaining signal component is representative of the hardness of the sample. The positioning of the sensor relative to the sample, as well as the measurement of hardness, are effected under microprocessor control. According to another feature of the present invention, the sensor is not only adjusted automatically in the "lift off" axis relative to the sample under test, but also in the tangential axis in order to produce repeatable and accurate measurement for curved surface cartridge cases.

It is therefore an object of the present invention to provide an improved method and apparatus for measuring metal hardness.

It is another object of the present invention to provide an improved method and apparatus for measuring the hardness of cartridge cases.

It is a further object of the present invention to provide an improved method and apparatus for measuring the hardness of cartridge cases on a high speed production basis.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DRAWINGS

FIG. 1 is a perspective view of a hardness tester according the present invention, FIG. 2 is a front view of a cartridge case that may be tested in accordance with the present invention, FIG. 3 is a schematic representation of a test reference reflection probe configuration as used in accordance with the present invention, FIG. 4 is a side view of such probe, FIG. 5 is an end view of the same probe, FIG. 6 is a perspective view illustrating the relative positioning between an eddy current probe and the cartridge case being tested, FIG. 7 is an end view of such probe and cartridge case, FIG. 8 is a plot of lift off and tangent loci for relative movement between a probe and a cartridge case, FIG. 9 is a block diagram of signal processor circuitry according to the present invention, FIG. 10 is a block diagram of control circuitry according to the present invention, and FIGS. 11–14 are flow charts depicting the automated procedure in accordance with the present invention.

DETAILED DESCRIPTION

Figure 10:
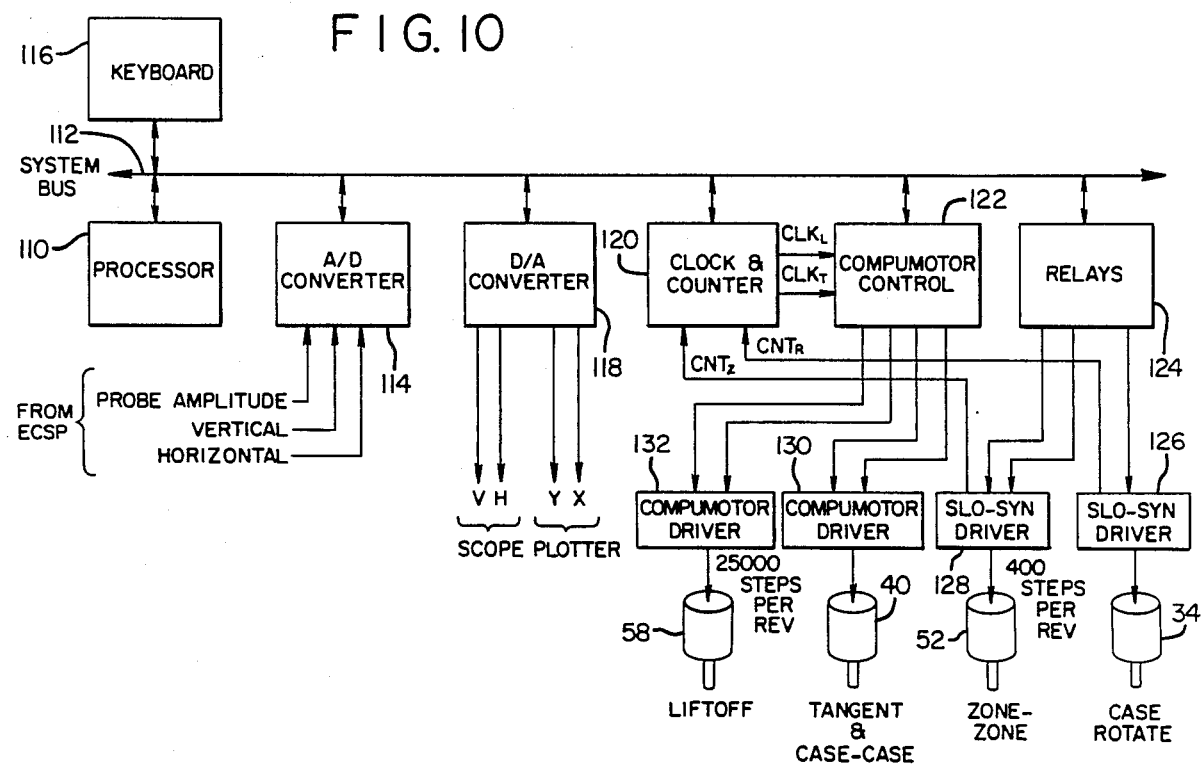

Referring to the drawings and particularly FIG. 1 illustrating a hardness tester in accordance with the present invention, a carriage 12 is employed to move plural cartridge case samples 14, 16 and 18 in a direction substantially tangential to eddy current probe 20. The cartridge cases are chucked for testing on rotary spindles 24, 26 and 28 provided with end caps 30, 32 for receiving the cases. The spindles are rotatable with respect to carriage 12 by means of sprockets 22 driven by a motor 34 which is also mounted on the carriage.

Carriage 12 is secured on horizontal slide 36 movable in a "tangential" direction along rails 38 under control of motor 40. The threaded shaft 42 of motor 40 engages threaded member 44 attached to slide 36 whereby rotation of the motor shaft urges slide 36 and carriage 12 in a direction tangential of the cartridge case.

Eddy current probe 20 is carried by mounting block 46 adjustably secured to the lower forward corner of signal processor module 48, the latter being movable in a vertical direction along rails 50 as determined by rotation of "zone" motor 52 through an intermediate screw mechanism (not shown). Motor 52 in the effect moves probe 20 in a direction longitudinal of the respective cartridge cases 14, 16, 18.

Rails 50 are in turn supported on slide 54 movable in a "lift off" direction along horizontal rails 56, i.e., in a direction perpendicular to cases 14, 16, 18. Motor 58 has a threaded shaft 60 engaging threaded member 62 secured to slide 54 whereby rotation of motor 58 is capable of driving probe 20 toward and away from one of cases 14, 16, 18.

With the cases 14, 16, 18 mounted as shown on spindles 24, 26, 28, rotation of motor 40 is effective for selecting one of the cases, i.e., placing one of the cases in juxtaposition with the end of probe 20, and also for procuring a desired tangent point whereby the end of probe 20 is closest the selected case. Motor 58 is rotated in order to place probe 20 at the desired lift off position with respect to the chosen case. Operation of motor 52 selects the "zone" along the case where the hardness is to be measured, while rotation of motor 34 will rotate the case such that hardness may be ascertained at the various locations therearound.

A typical 5.56 mm, M-193 brass cartridge case is illustrated in FIG. 2, depicting various zones or positions therealong where the hardness of the case is suitably measured. In the instance of each zone, representing a longitudinal distance from one end of the case, the case can be rotated whereby the hardness is determined at various angles around its periphery.

The probe 20 is further illustrated in FIGS. 3-7. Referring particularly to FIG. 3 depicting the probe's electrical connection, the probe is of the test reference reflection type comprising a pair of drive coils 64 and 66 connected in series, and a pair or sense coils 68 and 70 respectively disposed in flux linking arrangement with coils 64 and 66. The coils 64 and 66 are driven from a constant amplitude a.c. (sinusoidal) current source, which in turn generates a constant component of flux in each drive coil linking respectively with the secondary sense coils 68 and 70. This flux generates a constant sinusoidal amplitude voltage in coil 68, called a test coil since it is closest to cartridge case 18, and in reference coil 70 disposed at a distance along the probe from the case. Data are developed by this configuration when the coils 64, 68 are close enough to the case wall such that the drive coil 64 provides flux linking with the wall. The flux generates eddies of current in the brass case which in turn generate their own component of flux linking back into the test coil and altering the voltage generated in it as compared with the voltage produced in the reference coil 70, not affected materially by case 18. The eddy currents generated are highly dependent upon the material's conductivity, which is in turn affected by its work-hardened condition. This relationship allows the measurement of case brass hardness with eddy current instrumentation.

Referring particularly to FIGS. 4 and 5, the probe is rectangular in cross section and suitably formed of quartz. The long axis of the rectangular probe face (in FIG. 5) is oriented in the same direction as the longitudinal axis of the cartridge case to be measured. The typical long axis dimension of the probe face is 0.08 inches, which is small enough not to be influenced by either the shoulder or the mouth edges in zone 7 (FIG. 2) and yet large enough to provide the appropriate eddy current sensitivity for hardness measurement. The probe cross section is suitably 0.04 inches in width. The rectangular configuration (as opposed to cylindrical) and small size optimizes the accuracy and repeatability of the probe/case positioning and measuring sequence as hereinafter more fully discussed.

Each drive coil, 64 and 66, suitably consists of 14 turns of number 44 insulated wire close wound over the corresponding sense coil, 68, 70. The drive coil inductance is approximately 0.7 microhenry. Each sense coil 68, 70, suitably consists of 16 turns of number 44 insulated wire wound over the quartz probe body, which provides approximately 0.8 microhenry of inductance in each instance. It is understood these specifications are given by way of example and not by way of limitation. Coils 64, 68 are located substantially at the outer end of the probe for positioning adjacent the sample cartridge case, while coils 66, 70 are disposed approximately 0.14 inches back along the probe body. The relationship and approximate relative sizes of the probe and case are illustrated in FIGS. 6 and 7 together with the axes of relative probe and case movement as executed for accurate repositioning and measurement purposes according to the present invention.

It is known that the voltage induced in the sense coils of such a probe as a result of the alternating current magnetic field produced by the drive coils will have components which differ in phase and contain different kinds of information. It is possible to isolate phase information in the sense coils which relate to the relative positioning of the sense coils and the cartridge case from information indicative of the conductivity of the cartridge case. Thus, if sense information is detected with respect to two properly chosen orthogonal axes, and the probe is physically moved, the movement can be primarily detected in one axis, i.e., in a "horizontal" axis in FIG. 8 where curve 72 represents a "lift off" locus, i.e., for movement toward and away from the case. Curve 74, on the other hand, represents a "lift off" locus taken in measuring eddy currents for a cartridge case having a different (and lesser) hardness. Thus, the reading along each such locus in the horizontal axis in FIG. 8 is substantially proportional to lift off, while a reading in the vertical direction is proportional to cartridge case conductivity and therefore to hardness. Circuitry employing these properties for probe positioning and hardness measurement is further illustrated in FIGS. 9 and 10.

Referring particularly to FIG. 9, illustrating an eddy current signal processor circuit, a forty megahertz oscillator 76 drives a frequency divider and phase shift circuit 78 which provides a first ten megahertz, non-frequency shifted output at lead 80 and a second ten megahertz, 90° shifted output on lead 82. The outputs on leads 80 and 82 are applied to mixer circuits 84 and 86 respectively. The non-shifted output on lead 80 is also coupled to variable delay circuit 88 which is controllable so as to provide a variable phase-shifted output for application to current driver amplifier 90 by way of ten megahertz bandpass filter 92. Current driver 90 supplies the drive for coils 64 and 66 in series with respect to circuit ground.

The output of sense coils 68 and 70 in series is applied across a bridge circuit 94 made up of potentiometers 96 and 98 in parallel. The movable tap of potentiometer 96 is grounded and also coupled to the interconnection between sense coils 68 and 70, while the movable tap of potentiometer 98 is coupled to preamplifier 100 for providing an input to amplifier 100 with respect to ground. The output of coil 70 supplies a temperature stable reference used essentially to null the output of test coil 68 when the probe 20 is positioned at a desired lift off (e.g. fifteen to twenty thousandths of an inch) with respect to a standard cartridge case, preferably at zone 5 representative of the approximate center of the case hardness spread. Preamplifier 100 is coupled to the input of mixer driver 102 via ten megahertz bandpass filter 103. Potentiometers 96 and 98 are adjusted for a minimum ten megahertz signal at the output of mixer driver amplifier 102. As a result of bridge balance, changes in the output of driver 102 attributable to the influence of eddy currents in the cartridge case under test on the probe can be detected.

The output of driver 102 is applied to mixers 84 and 86, and also to amplitude detector 104 for providing an overall probe amplitude signal. Mixer 84 drives amplifier and low pass filter 106 while mixer 86 drives amplifier and low pass filter 108. The outputs of elements 106 and 108 are respectively designated the horizontal output signal and the vertical output signal. This circuitry enables quadrature detection in response to mixing of the probe output signal from driver 102 with zero and 90° reference signals on leads 80 and 82 respectively, developed from the same source as the probe drive. The mixers thus yield signals that, when low-pass filtered by circuits 106 and 108, represent the rectangular coordinates of the alternating current probe output signal. The lift off locus and the conductivity or hardness locus are separated by phase on the complex impedance plane. The lift off locus can thus be oriented or rotated onto one orthogonal axis, e.g. the horizontal axis, while the remaining or vertical component is substantially lift off independent and can be used to measure hardness. The proper orientation of the respective components is accomplished through adjustment of the phase of the probe drive by adjusting the variable delay of circuit 88 as hereinbelow indicated. The phase of each of the reference signals on leads 80 and 82 could have been adjusted, but it has been found advantageous and simpler to adjust the drive phase in the manner illustrated.

While the bridge 94 is balanced as hereinbefore set out, nulling signals are also applied to each of elements 106 and 108, with the probe positioned at desired lift off over the aforementioned standard cartridge case, whereby the horizontal and vertical outputs are substantially nulled. Then, variable delay 88 is adjusted so that the lift off locus lies substantially on the horizontal axis with increasing lift off presenting a negative going signal and decreasing lift off presenting a positive going signal. Reference is again made to FIG. 8 wherein a typical lift off locus is represented at 72.

The FIG. 8 display can be derived by applying the horizontal signal from circuit 106 to the horizontal drive of an oscilloscope, and the vertical signal from circuit 108 to the vertical drive of an oscilloscope, followed by movement of the probe in the lift off direction perpendicular to the cartridge case sample. A change in one signal component is the primary result of probe movement, without much change in the orthogonal component. However, if another cartridge case is substituted, e.g. having lower hardness, a different result is produced as exemplified by the shift from curve 72 to curve 74. As indicated above, phase adjustment with variable delay circuit 88 is accomplished so that movement of the probe in a direction toward and away from the sample primarily produces the horizontal trace without much change vertically on the oscilloscope screen.

The outputs of the eddy current signal processor circuit of FIG. 9 are applied to the microprocessor operated position controller and output circuit of FIG. 10. Referring to FIG. 10, processor 110, suitably comprising a Zilog Z-80 microprocessor, is connected to a system bus 112 and is provided with conventional memory means (not shown). Also connected to bus 112 is an analog-to-digital converter 114 receiving the amplitude, vertical and horizontal signals from the circuit of FIG. 9, whereby these signals are converted to digital form that can be used by processor 110. A keyboard 116, which may be in the form of a terminal including a display, is additionally coupled to system bus 112, together with a digital-to-analog converter 118 suitably driving an oscilloscope or alternatively supplying X and Y signals to a plotter.

Bus 112 is further connected to clock and counter 120, compumotor control 122 and relay group 124. Relays 124 are employed for turning motors 34 and 52 off and on by way of SLO-SYN driver 126 and SLO-SYN driver 128 respectively. Motors 34 and 52 are stepper motors operating at 400 steps per revolution and are controlled by SLO-SYN drivers 126 and 128 which are commercially available. Under processor control, a relay of group 124 turns on driver 126 causing motor 34 to rotate in response to stepping signals generated internally by driver 126. The stepping signals are counted by clock and counter 120 which receives $CNT_R$ as an input from driver 126, and when the desired rotation has been achieved in accordance with a command from processor 110, clock and counter 120 signals the processor. In response, the energizing relay in group 124 will turn off driver 126 whereby motor 34 will come to a stop. As heretofore described, motor 34 is effective in rotating cartridge cases 14, 16, 18 on spindles 24, 26, 28. Motor 34 rotates in only one direction.

In a similar manner, a relay of group 124 (under processor control) will turn on driver 128 which operates motor 52 at 400 steps per revolution in one of two directions. Clock and counter 120 receives the stepping signal as $CNT_Z$ generated by driver 128 and signals the processor when the desired revolution of motor 52 has been achieved. Thereupon, the relay providing an input to driver 128 is de-energized. Motor 52 can be operated in either of two rotational directions and correspondingly two input leads are shown from relay group 124 to driver 128. As hereinbefore mentioned, motor 52 is utilized in moving the probe 20 between the various zones along a particular cartridge case.

Compumotor control 122 is of conventional design and is employed for providing a signal on one of two leads to compumotor driver 130 for rotating motor 40 in one of two directions, and for providing a signal on one of two leads to compumotor driver 132 for causing motor 58 to rotate in one of two directions. In this instance clock and counter 120 provides stepping pulses for motors 40 and 58 respectively via compumotor control 122, and compumotor control 122 supplies the number of such pulses, under processor control, for bringing about the commanded rotation of motors 40 and 58 respectively. Each of motors 40 and 58 executes 25,000 steps per revolution and hence the positioning achieved therewith is more accurate than the positioning achieved by means of 400 step motors 34 and 52.

Each of the motors 40 and 58 is commercially available together with the compumotor driver therefor.

Clock and counter circuit 120 is processor controllable in regard to the frequency of the clock pulses $CLK_L$ and $CLK_T$ produced thereby and supplied to compumotor control for coupling to the respective compumotor drivers. For instance, the signal $CLK_L$ is variable in frequency under processor control for varying the speed of rotation of lift off motor 58.

Considering overall operation of the present invention, it will be appreciated that accurate hardness data is to be produced and the time required to make each measurement is to be minimized. In order to perform rapid measurement with respect to thin walled cartridge case material, the eddy current operating frequency employed is fairly high, e.g. at least ten megahertz, and signal processor amplification gains are high so that signal components related to sample hardness and position are significant after balancing and nulling portions of the signal drive which do not carry the desired information by means of the circuit of FIG. 9.

Especially inasmuch as a relatively high operating frequency and relatively high gain signal processing is being employed, it is highly desirable that probe-to-material positioning be highly accurate and repeatable, since tenths of a percent conductivity need to be resolved. In the situation where the material is a thin walled curved surface, such as presented by a 5.56 mm, M-193 cartridge case, the probe should be repeatedly positionable over the sample surface to within ±3 microns of a nominal predetermined position. In order to secure repeatable measurement in a short time cycle, the controller of FIG. 10 rapidly reads the probe output signals and processes them for positioning the probe in a closed loop manner, and then processes the signals for the immediate generation of hardness data. The probe may thus be thought of as self-adjusting.

Referring again to the apparatus of FIG. 1, one of the cartridge cases, e.g. cartridge case 14, is desirably a calibration standard the hardness of which is already known. The circuit is suitably calibrated in the manner hereinafter more particularly described.

In initially setting up the apparatus, the probe 20 is located at a predetermined position relative to a standard cartridge case, e.g. at a spacing of approximately fifteen to twenty thousandths of an inch from a cartridge case as determined manually, for instance with a feeler gauge. The probe is positioned as closely as possible at a tangent point closest to the curved wall of the cartridge case so that the forward face of the probe is substantially parallel to a plane tangent to the sidewall of the cartridge case and the longitudinal axis of the probe would intersect the longitudinal axis of the cartridge case as illustrated by way of example in FIG. 7. The bridge 94 is then balanced. The "horizontal" output is nulled and phase rotation is adjusted by means of variable delay circuit 88 in FIG. 9 so that the lift off locus (as depicted in FIG. 8) lies substantially on the horizontal axis with increasing lift off indicated in the negative direction and decreasing lift off indicated in the positive direction. The vertical signal is "nulled" whereby there is a fairly even spread across the amplifier 108 output for the range of hardness being tested. Having set up the apparatus, and having established the predetermined position of the probe which will be repeated during subsequent measurements, the system is then operated automatically.

For the automatic procedure, it will be assumed the initial set up has already been performed, and three cartridge cases are inserted on respective spindles as illustrated in FIG. 1. Furthermore, it is assumed one of the three cartridge cases is always a calibration standard, the hardness values for which are known. Calibration is suitably accomplished with the calibration standard cartridge case in first position, e.g. in the position as indicated at 14 in FIG. 1. The probe is positioned at zone 1 for the cartridge case where vertical data are read=Vert1. The probe is then positioned at zone 7 where vertical data are read=Vert7. A constant M is calculated as $$M = (DPH1 - DPH7)/(Vert1 - Vert7) \qquad [1]$$

Finally a constant B is calculated as $$B = DPH1 - M*Vert1 \qquad [2]$$

In these expressions, DPH1 and DPH7 are known diamond point hardnesses at zone 1 and zone 7 of the calibration standard cartridge case. Using the constants M and B as calculated above, the hardness for other readings can be calculated from the vertical signal as follows.

$$DPH = M*Vert + B \qquad [3]$$

It is seen the hardness is a function of only the vertical signal. The calculation procedure is carried out by processor 110 as hereinafter more fully described. Although three cartridge cases, 14, 16, 18, are illustrated in FIG. 1, where one of these is the calibration standard, it will be understood a larger number of cartridge cases are suitably accommodated on carriage 12, but one of these should in any case comprise a calibration standard. After the calibration procedure, the system proceeds to take measurements for the hardness of cartridge cases 16 and 18.

After initial set up, the probe will be positioned automatically with respect to the calibration standard and with respect to cartridge cases the hardness of which are to be measured. In an at rest position, e.g. before positioning adjacent a cartridge case, or before movement in between cartridge cases, the probe is suitably "backed off" to a distance approximately fifty thousandths of an inch away from the location of a cartridge case outer wall. The lift off of the probe is then automatically adjusted such that the probe will subsequently be located at an accurately predetermined lift off with respect to the cartridge case as was determined during initial set up.

Motor 40 is operated under computer control such that the spindle carrying the desired cartridge case 14, 16 or 18 is an approximate juxtaposition with the probe 20. Motor 58 is then actuated for bringing the probe 20 into the aforementioned predetermined position at least in the lift off direction. At first, during "coarse" positioning, the speed of motor 58, under control of clock and counter circuit 120 and processor 110, is substantially proportional to lift off and decreases as the predetermined lift off point is approached. At this time, the probe amplitude from amplitude detector 104 can be monitored and when the amplitude signal decreases to about two or three volts, the "horizontal" signal from amplifier 106 is monitored. Coarse and fine adjustments are employed inasmuch as the fine adjustment desirably employs high gain for the horizontal signal to provide enchanced sensitivity. This signal is useful near the predetermined desired lift off and the lift off motor speed continues to be substantially proportional to lift off until the horizontal signal detected is near its present null within predetermined limits. Liftoff movement is continued on a fine adjustment basis at a slower speed until the null is substantially reached.

Although the probe 20 will be in substantial juxtaposition with the curved cartridge case under investigation as a result of case-to-case movement executed by motor 40, it is now important that the probe be positioned at the correct tangent point in order that repeatable testing can be carried out. Therefore, after movement of probe 20 in the lift off direction under the control of motor 58 to substantially the null position, motor 40 is again operated under processor control whereby the correct tangent point is reached. The horizontal position signal or lift off signal is also used as a measure of the desired tangent positioning.

A typical tangent locus is illustrated at 134 in FIG. 8, wherein such tangent locus can be generated by physical movement of carriage 12 in the tangent direction while the horizontal and vertical outputs from amplifiers 106 and 108 are applied to the horizontal and vertical drives of an oscilloscope. It can be seen that the tangent locus, though primarily in the horizontal direction, does contain a vertical component that if not minimized could cause an error in the readings used to calculate hardness. It is therefore important to the hardness measurement accuracy and repeatability that the probe's tangential position over the case's curved surface be repeatable. To accomplish this end, the horizontal signal is monitored while the case is moved in tangential position. The controller circuitry of FIG. 10 selects the motor direction that causes the horizontal signal from amplifier 106 in FIG. 9 to move in the positive direction (to the right in FIG. 8). If the signal is detected moving in the negative direction, the rotational direction of motor 40 in FIG. 1 is reversed. This sequence is allowed to occur for several motor reversals in order to minimize the possibility of noise causing a significant setting error. The optimum probe position is indicated when the horizontal signal is at the most positive point (farthest point to the right) at 136 on the tangent locus. After the control circuit of FIG. 10 directs plural reversals of motor 40 under control of processor 110, the point 136 will have been reached.

It will be seen the position of the probe has been substantially optimized in both the lift off and the tangential directions. However, the point 136 as illustrated in FIG. 8 for the tangential locus is somewhat to the right of the null point for the lift off locus. Therefore, another lift off adjustment is suitably made under processor direction until the horizontal null is again reached.

When the probe is thus finally positioned at the predetermined standardized location, the vertical signal from amplifier 108 may now be processed in accordance with the aforementioned expression, DPH=M*Vert+B, to provide the hardness data for the point on the cartridge case under examination. The same procedure is followed for other zonal points along the cartridge case, and it may be desired to rotate the cartridge case to provide plural hardness readings at each zone. Thus, motor 34 is suitably rotated for making hardness measurements at 90° intervals around each cartridge case, it being unnecessary in general to "back off" the probe between measurements in one zone. To switch from zone to zone, the probe may be backed off by means of motor 58 after each measurement and motor 52 is actuated for disposing probe 20 adjacent another zone where the above procedure is repeated. After all the desired measurements have been made with respect to one of the cartridge cases, e.g. case 16, motor 40 is operated to place cartridge case 18 in approximate juxtaposition with the probe and the measurement procedure is again repeated.

As hereinbefore indicated, the size of the probe and especially in direction of tangential movement is quite narrow in comparison to the size of the cartridge case. Also the probe is substantially rectangular in cross section. This size and configuration minimizes tangent movement effects on the vertical signal employed for deriving hardness information. The narrow, rectangular-shaped probe produces a better signal-to-noise ratio than a larger or a cylindrical-shaped probe, where hardness-related vertical data are considered to be the signal and tangent-related vertical data are considered to be the noise.

It is seen highly accurate and repeatable hardness measurements can be obtained with the system according to the present invention wherein eddy current hardness measurement is integrated with accurate and repeatable probe positioning in a closed-loop system. Of particular significance is the increase in speed at which measurement can be made. The initial system constructed was 12.5 times faster than the diamond-point indentation method heretofore employed and which has heretofore been the only measurement method capable of providing hardness data on small caliber cartridge cases. Microprocessor control enhances rapid movement and adjustment as well as flexibility in terms of inspecting metal geometries. The system is readily integrated into manufacturing in-process controls for cartridge cases or the like.

Referring now to FIGS. 11 through 14, the program control for the processor circuitry of FIG. 10 will be described. As will be appreciated by those skilled in the art, the flow charts depicted define a program by which processor 110 in FIG. 10 directs continued sample positioning together with hardness measurement subsequent to an initial set up of the system.

Referring to FIG. 11, the overall programming process will be considered wherein a calibration standard cartridge case is located on one of the spindles in FIG. 1, while at least one other cartridge case is carried by another spindle and constitutes a sample the hardness of which is to be measured. A test is initiated at 140 and the location of the probe at zone 5 of the calibration standard is directed as noted in block 142. SET PROBE routine 144 is then followed (as further depicted in FIG. 12 and following) for substantially duplicating the positioning performed at initial set up. Thereafter, the vertical signal is nulled at 146 to provide a fairly even spread over the amplifier output for the general hardness range. A NULL V input is provided to amplifier and low pass filter 108 in FIG. 9 under processor control.

The probe is then positioned at zone 7 of the calibration standard cartridge case in step 148 followed by once again accessing the SET PROBE routine at 150. The vertical data is then read at 152 to provide the Vert7 information for formula [1] supra.

In step 154 the probe is located at zone 1 of the calibration standard cartridge case and the SET PROBE routine is entered at 156. Following the correct positioning of the probe, the vertical data is read as indicated at 158 to provide the Vert1 information for use in expressions [1], [2] above. In step 160 in FIG. 11, the coefficients M and B are calculated in accordance with expressions [1] and [2], also using the known diamond point hardness values for the calibration standard.

In block 162 of the procedure in FIG. 11, the probe is located at the appropriate case, and along the case at an appropriate zone test point, such case being other than the calibration standard. In step 164, the SET PROBE routine is executed again, while according to block 166 the vertical data is read from amplifier and low pass filter 108. Employing the vertical data read as Vert in expression [3] supra, the diamond point hardness for the selected test point is computed in step 168.

In decision block 170, it is determined whether more test points at further zones of the sample are to be tested according to predetermined procedure, and if they are, then return is made to block 162 and the probe is moved longitudinally by means of motor 52 to another zone, or if more points are to be tested in the same zone, the case under test is first rotated to the desired position by means of motor 34. If one or more additional cartridge cases are to be tested, then the indication from decision block 170 will be yes and return will be made to block 162 for locating the probe with respect to another case. After all the test points which are to be measured have been reached, program block 172 may be entered where the test results are generated and displayed, or printed by appropriate means (not shown) under control of processor 110. The overall procedure for a given sample cartridge case or plural cartridge cases on carriage 12 is now concluded.

Figure 12:
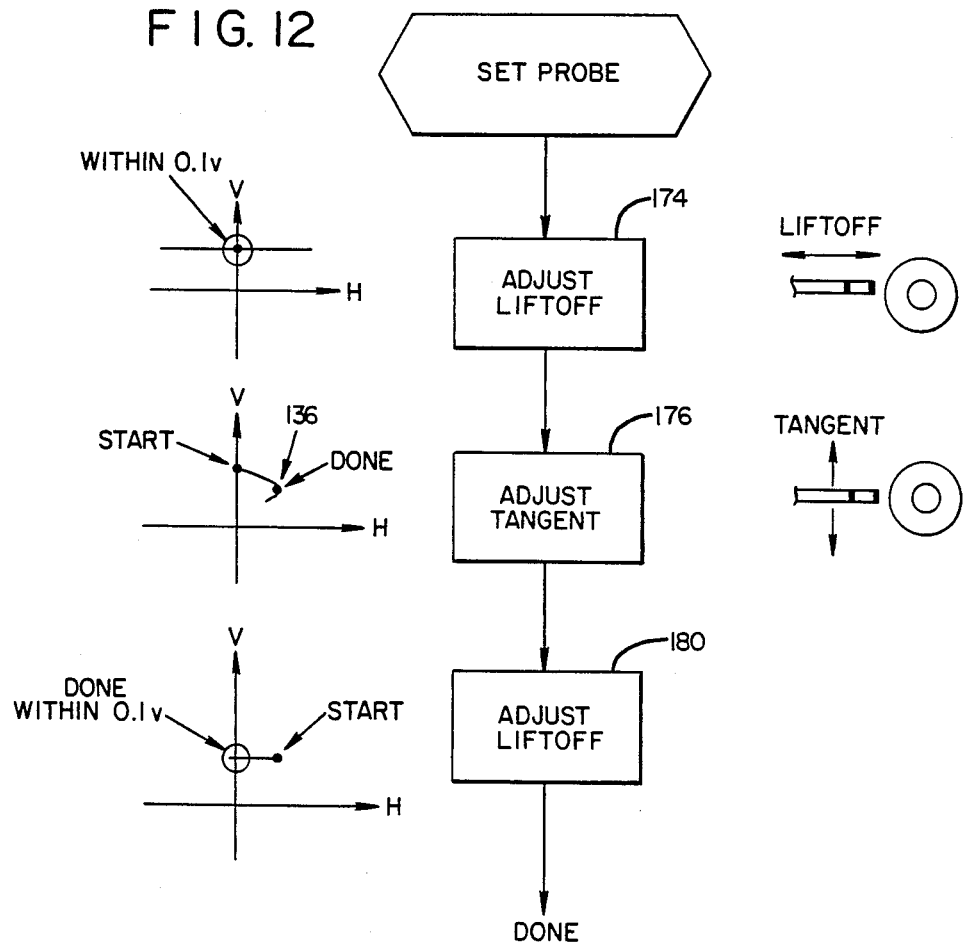

The SET PROBE routine is outlined in FIG. 12. The overall procedure first includes ADJUST LIFT OFF in block 174 followed by ADJUST TANGENT in block 176, after which ADJUST LIFT OFF is again performed in block 180. As depicted in the drawing to the left of ADJUST LIFT OFF block 174, lift off is adjusted until the horizontal signal (depicted along the lift off locus) is within 0.1 volts of horizontal null. Then, as shown to left of ADJUST TANGENT block 176, the tangent positioning is undertaken until optimum tangent point 136 is reached as hereinbefore indicated. After ADJUST TANGENT, ADJUST LIFT OFF is again employed for reaching the horizontal null. At this time, the probe is considered positioned at the predetermined standard location with respect to the point on the cartridge case where hardness is to be measured. Return is made to be main program of FIG. 11

Figure 13:
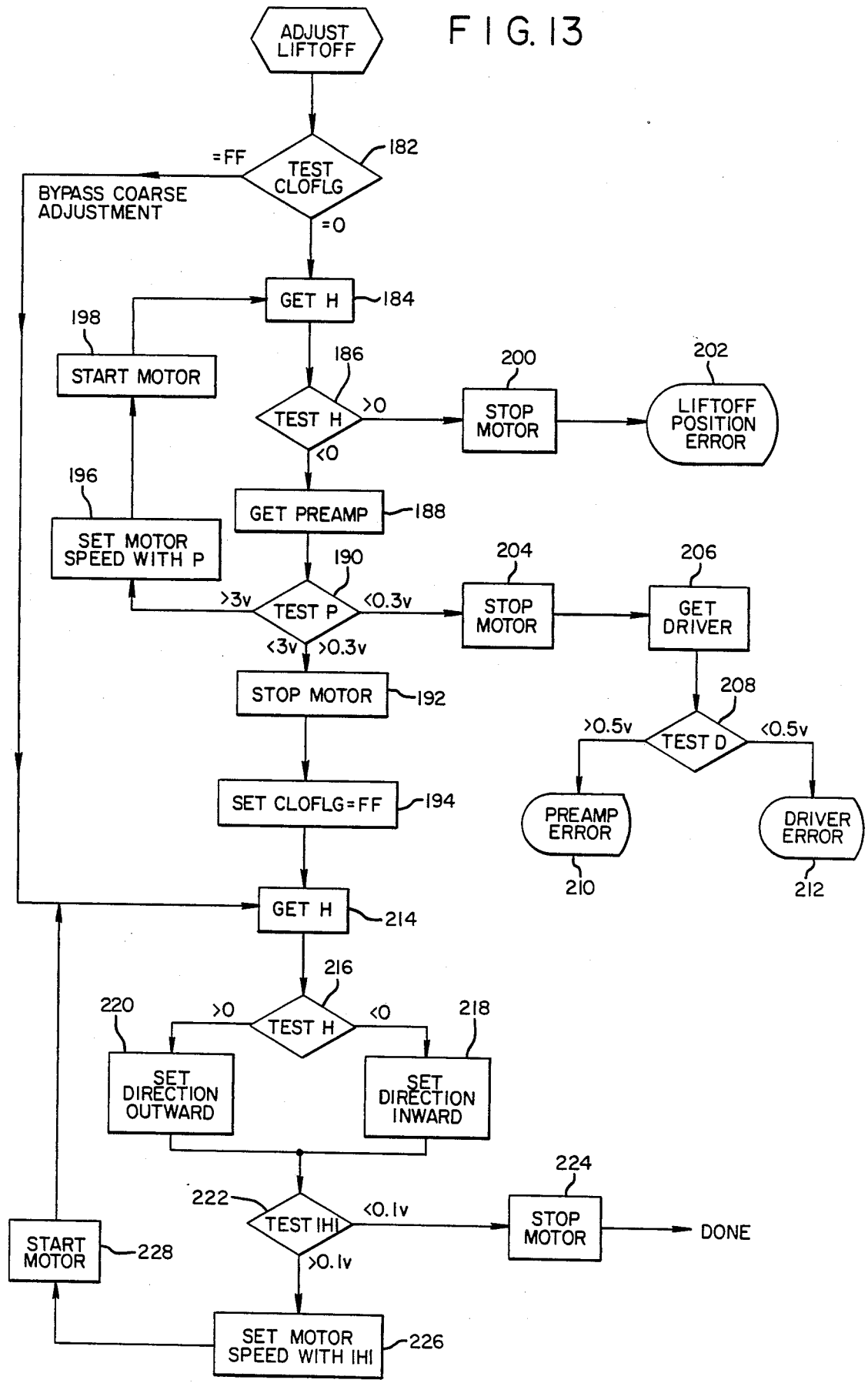

In FIG. 13 the ADJUST LIFT OFF routine is more fully depicted. A coarse lift off flag, CLOFLG, is maintained by the processor to distinguish coarse lift off, wherein the probe is greater than a predetermined distance from the sample, and more accurate lift off movements at a lower speed when the probe is close to the sample. The coarse lift off flag is tested at 182 and if the same is zero, indicating the probe is still in the coarse lift off region, the processor accesses the horizontal signal in block 184, testing the same in decision block 186 to determine whether the horizontal signal is greater than or less than zero. If it is less than zero such that it is determined the probe is farther away from the sample case than the null point, the output of preamplifier 100 is accessed according to block 188 and tested in decision block 190. If the output of preamplifier 100 is within the range of 0.3 volts to 3 volts, the probe is determined to be in the fine adjustment range and the lift off motor 58 will be stopped in block 192. The coarse lift off flag CLOFLG is set to FF in block 194.

If, on the other hand, the result of the test in decision block 190 is that the output of preamplifier 100 is greater than 3 volts, whereby the probe is considered to be in the coarse lift off region, the speed of motor 58 is set in step 196 according to the value of P, the preamplifier output, so that the motor speed will be substantially proportional to lift off. The lift off motor 58 is started in step 198 and the horizontal signal is again accessed in step 184 for test in step 186.

If decision block 186 indicates H is greater than 0, i.e., that the probe is closer to the sample cartridge case than the desired position, the motor 58 is stopped according to block 200 and a lift off position error will be signaled at 202. That is, according to operation of the system, the probe should not be closer to the test sample than the desired position, at least at this point in the procedure, without a software or hardware error. Also in decision block 190 if the preamplifier output is less than 0.3 volts, motor 58 is stopped in block 204 and the output of driver 102 is accessed in block 206. The driver output is tested at 208 and if the same is greater than 0.5 volts, a preamplifier error is noted at 210. That is, if the driver is operating correctly its output will be greater than 0.5 volts and therefore the preamplifier output must be an error. On the other hand, if the driver output is less than 0.5 volts, a driver error would appear to be the case.

Returning to the main ADJUST LIFT OFF program flow, after setting CLOFLG to FF in block 194, signifying the lift off movement is within the fine adjustment region, the horizontal signal is accessed at 214. Also, if the test of CLOFLG indicated FF in decision block 182, similarly denoting probe position in the fine adjust region, block 214 would again be entered and the coarse adjustment in steps 184-198 would be bypassed. After the horizontal signal is accessed at 214, the same is tested in decision block 216 to determine whether it is less than 0, signifying the probe is farther from the cartridge case than the null point, or greater than 0, indicating the probe is closer to the cartridge case than the null point. If the result of the test is less than 0, the direction of motor 58 is set for inward movement in step 218, while if the result of the test is greater than 0, motor 58 is set for outward movement in block 220. The absolute value of the horizontal signal is then tested at 222. If such value is less than 0.1 volts, the motor 58 is stopped at 224 since the probe is considered to be located at the desired lift off null point. If the result of the test 122 is greater than 0.1 volts, the speed of motor 58 is set in accordance with the value of H at 226 and the motor is started in block 228. Return is made to block 214 and the the probe position is again tested in the intervening steps until the procedure is completed.

Figure 14:
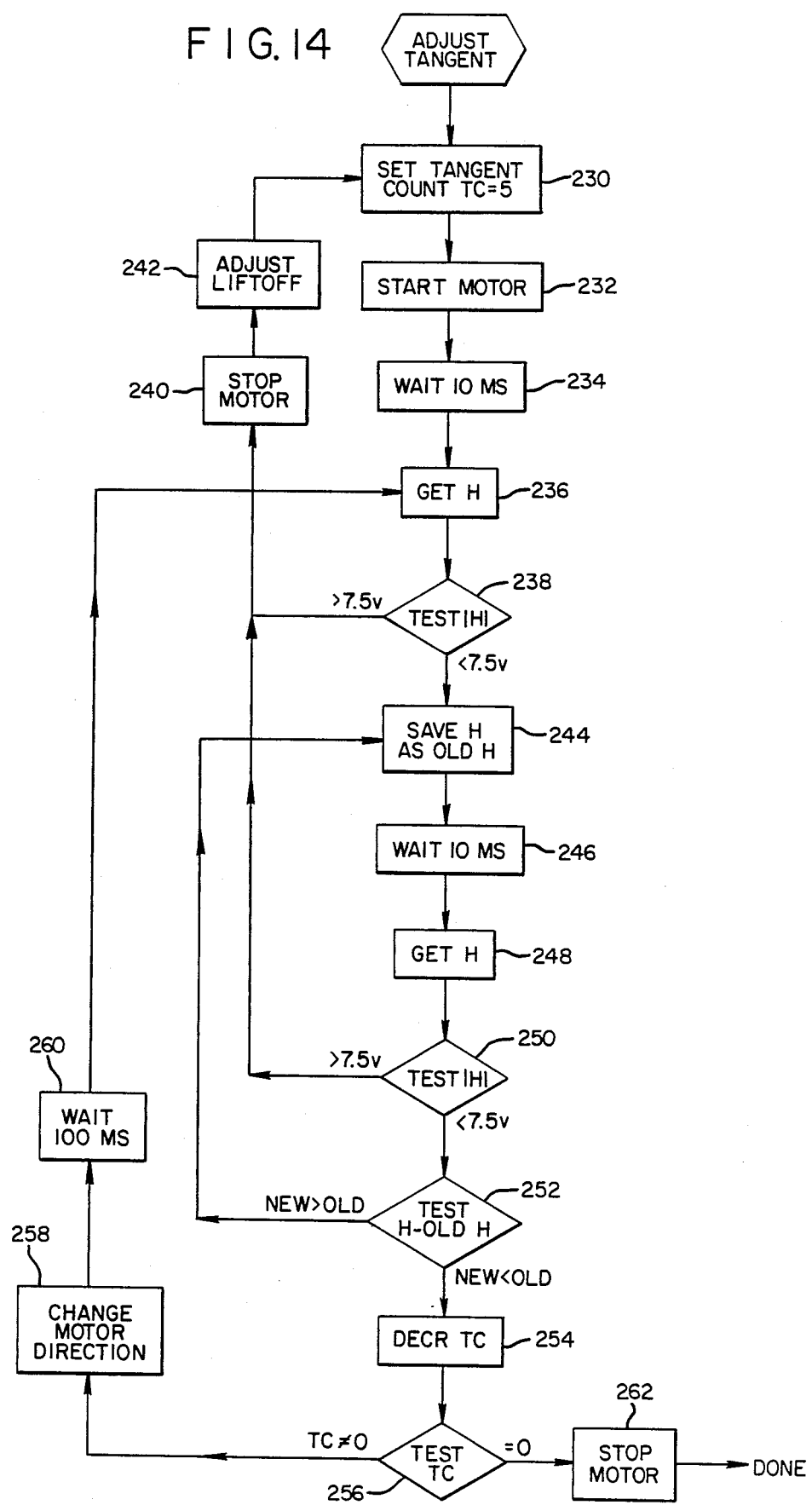

Turning now to FIG. 14, detailing the ADJUST TANGENT procedure, a tangent count is first set for predetermining the number of motor reversal iterations which will be employed to reach optimum tangent point 136 (in FIGS. 8 and 12). For example, the tangent count is suitably set to five in step 230. Motor 40 is then started at 232 and a delay of ten milliseconds is allowed at 234 whereby some initial movement of carriage 12 in the tangential direction may take place. In step 236, the horizontal signal is accessed after which its value is tested in decision block 238. If the horizontal signal is greater than 7.5 volts, a lift off adjustment is apparently required and the motor 40 is stopped according to block 240. An ADJUST LIFT OFF routine is then repeated at 242 with return to block 230.

If the value of H as tested in block 238 is less than 7.5 volts, the value of H is saved as the "old H" as noted at 244. Another ten millisecond delay takes place in block 246 after which the horizontal signal is accessed at 248 and tested in decision block 250. If the value of the horizontal signal is now greater than 7.5 volts, motor 40 is stopped and the lift off is adjusted as before. If the value of H is less than 7.5 volts, the old H is subtracted from the new H as indicated in decision block 252. If as a result of the subtraction it is seen the new H is greater than the old H as would signify movement in the positive direction along tangent locus 134 in FIG. 8 toward optimum point 136, then the procedure of steps 244-252 is repeated. If the new value of H is less than the old value of H, signifying a change in direction of movement along the tangent locus, the tangent count is decremented at 254 and tested in block 256. If the tangent count is 0 denoting a predetermined number of changes in motor direction have occurred, motor 40 is stopped at 262 and return is made to the main program. If the tangent count is not 0, the motor direction is changed as indicated in block 258. After a delay of 100 milliseconds to allow the motor reversal to settle, the horizontal signal is again accessed at 236 and the procedure is repeated until the tangent count is 0. As hereinbefore described in connection with FIG. 12, after ADJUST TANGENT, the ADJUST LIFT OFF routine is repeated for accurate positioning of the probe at a predetermined position in order to facilitate an accurately repeatable hardness reading. As a result of the closed loop microprocessor control system, the positioning of the probe can be carried out very rapidly as well as very accurately, facilitating production line vesting of cartridge cases or similar objects.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method for testing the hardness of a metallic sample having a surface, comprising:
    inducing eddy currents in said sample with a probe generating an alternating current magnetic field,
    providing a signal produced by the eddy currents in said sample,
    automatically adjusting the positioning of said probe in a direction perpendicular to the surface of said sample in response to a parameter of said signal,
    automatically adjusting the positioning of said probe in a direction tangential to the surface of said sample in response to a parameter of said signal, and
    employing a parameter of said signal as a measure of said hardness.

2. The method according to claim 1 including sensing the eddy currents produced in said sample with said probe.

3. The method according to claim 2 wherein the eddy currents are induced in said sample at a frequency of at least approximately 10 MHz.

4. The method according to claim 1 including:
    detecting phase-separated components of said signal related to conductivity of said sample and related to the position of said probe,
    employing said component related to the position of said probe to adjust said perpendicular positioning of said probe to a standardized lift off location,
    employing said component related to the position of said probe to adjust said tangential positioning of said probe to a standardized tangential location, and
    employing a said component related to conductivity as said measure of hardness.

5. The method according to claim 4 wherein said phase separated components are orthogonal components.

6. The method according to claim 5 including adjusting said detection of phase separated components so that information pertaining to conductivity is detected with respect to one orthogonal axis while information pertaining to position is detected with respect to the remaining orthogonal axis.

7. The method according to claim 1 for testing the hardness of a sample wherein the surface of the sample is curved.

8. The method according to claim 1 including sequentially testing the hardness of samples wherein the hardness of one of said samples is known and used for correlating eddy currents with hardness for other samples.

9. A method for testing the hardness of a cartridge case having a curved surface, comprising:
    inducing eddy currents in said case with a probe generating an alternating current magnetic field,
    sensing eddy currents produced in said case including providing a signal in response to said eddy currents, and detecting phase-separated components of said signal produced by the eddy currents related to the conductivity of said case and related to the position of said probe,
    automatically adjusting the positioning of said probe relative to said case in response to parameters of eddy currents which are sensed in said case, including employing a said component responsive to the tangential position of said probe relative to said case to adjust tangential positioning of said probe relative to said case to a standardized tangential position,
    employing a said component related to conductivity as a measure of hardness, and
    repeating said method at zones along said cartridge case.

10. The method according to claim 9 further including rotating said cartridge case around its longitudinal axis for measuring hardness in zones around said cartridge case.

11. A method for testing the hardness of a metallic sample having a curved surface, comprising:
    inducing eddy currents in said sample with a probe generating an alternating magnetic field,
    sensing eddy currents produced in said sample to provide a signal related to conductivity of said sample and related to the position of said probe relative to said sample,
    detecting a component of said signal related to the position of said probe,
    automatically adjusting the position of said probe in response to said last mentioned component of said signal in a first direction perpendicular to said sample until a location of standardized lift off is substantially achieved, automatically adjusting the position of said probe in response to said last mentioned component of said signal in a second direction tangential to the surface of said metallic sample until change in said last mentioned component of said signal reverses direction at least once, detecting a component of said signal related to the conductivity of said sample, and employing said component related to the conductivity of said sample as a measure of hardness of said sample.

12. The method according to claim 11 wherein the position said probe is automatically adjusted in said second direction after being automatically adjusted in said first direction, and further including automatically adjusting the position of said probe in said first direction a second time after automatically adjusting the position of said probe in said second direction.

13. A method of testing the hardness of a metallic sample, comprising:

inducing eddy currents in said sample with a probe, sensing said eddy currents induced in said sample and producing a signal in response thereto, separating said signal into components related to the position of said probe relative to said sample, and related to the conductivity of said sample, automatically positioning said probe to a predetermined lift-off position in response to said component of said signal related to position, automatically positioning said probe to a predetermined tangential position in response to said component of said signal related to position, and converting said component of said signal related to the conductivity of said sample to an indication of hardness.

14. The method according to claim 13 wherein said separating of said signal is produced by detection of orthogonal components of said signal.

15. Apparatus for testing the hardness of a metallic sample having a surface, comprising:

movable probe means for inducing eddy currents in said sample, means for sensing the eddy currents induced in said sample and for generating a signal in response thereto, means for detecting components of said signal related to hardness of said sample and related to the position of said probe, first means for automatically positioning said probe in a first direction in response to said component related to position, second means for automatically positioning said probe in a second direction in response to said component related to position, and means for employing said component related to hardness as a measure of said hardness after said positioning of said probe.

16. The apparatus according to claim 15 wherein said means for sensing comprises a portion of the movable probe means.

17. The apparatus according to claim 16 wherein said movable probe means comprises a test reference reflection probe and wherein said apparatus futher comprises a bridge circuit providing a sensing output for said probe.

18. The apparatus according to claim 17 wherein said detecting means comprises means for detecting said components orthogonally.

19. The apparatus according to claim 15 wherein said component related to position is responsive to probe lift off relative to said sample, and wherein said first means for automatically positioning comprises means controlled by the last mentioned component to position said probe means to a location of standardized lift off.

20. The apparatus according to claim 15 wherein said component related to position is responsive to the tangential location of said probe means relative to said sample, and wherein said second means for automatically positioning comprises means controlled by the last mentioned component for adjusting said probe means to a standardized tangential location.

21. The apparatus according to claim 15 employed for testing the hardness of a metallic sample having a curved surface wherein said probe means is narrow in a direction tangential to said curved surface.

22. The apparatus according to claim 21 wherein said probe means is substantially rectangular in cross section.

23. Apparatus for testing the hardness of a metallic sample, comprising:

movable probe means having a test reference reflection probe for inducing eddy currents in said sample, and for sensing the eddy currents induced in said sample and for generating a signal in response thereto, a bridge circuit providing a sensing output signal for said probe, means for driving said probe means with an alternating current signal to cause said probe means to induce said eddy currents into said sample, means for detecting orthogonal components of said output signal related to hardness of said sample and related to the position of said probe including phase shift means also receiving the output of said drive means and providing a pair of signals having a ninety degree phase difference, first and second mixers, each combining the sensing output of said probe means from said bridge circuit with one of said pair of signals to produce first and second mixer outputs as said components related to hardness of said sample and related to the position of said probe means respectively, and means for adjusting the phase of the output signal of said drive means relative to said pair of signals, means for automatically positioning said probe in response to said component related to position, and means for employing said component related to hardness as a measure of said hardness after said positioning of said probe.

24. The apparatus according to claim 23 wherein said means for adjusting the phase comprises phase shift means interposed between the output of said drive means and said probe means.

25. The apparatus according to claim 24 wherein the last mentioned phase shift means comprises signal delay means.

26. A method of testing the hardness of a cartridge case having a curved surface, comprising:

inducing eddy currents in said case with a probe generating an alternating current magnetic field, sensing eddy currents produced in said case including providing a signal in response to said eddy currents and detecting phase-separated components of said signal produced by the eddy currents related to the conductivity of said case and related to the position of said probe, automatically adjusting the positioning of said probe relative to said case in response to parameters of eddy currents which are sensed in said case, including employing a component responsive to the tangential position of said probe relative to said case to adjust tangential positioning of said probe relative to said case to a standardized tangential position by iteratively moving said probe relative to said case in a tangential direction and reversing movement upon predetermined change of said component related to the tangential position of said probe, and employing a said component related to conductivity as a measure of hardness.

* * * * *

UNITED STATES PATENT AND TRADEMARK OFFICE
CERTIFICATE OF CORRECTION

PATENT NO. : 4,849,693

DATED : July 18, 1989

INVENTOR(S) : JAMES M. PRINCE et al

It is certified that error appears in the above-identified patent and that said Letters Patent is hereby corrected as shown below:

Column 3, line 39, "or" should be --of--.

Column 9, line 5, "present" should be --preset--.

Column 11, line 50, "be" should be --the--.

Column 12, line 51, "122" should be --222--.

Column 12, line 54, delete "the" (second occurrence).

Column 15, line 15, between "position" and "said" insert --of--.

Signed and Sealed this

Twelfth Day of April, 1994

Attest:

BRUCE LEHMAN

*Commissioner of Patents and Trademarks*

*Attesting Officer*